(12) United States Patent
Wang

(10) Patent No.: US 11,986,249 B2
(45) Date of Patent: May 21, 2024

(54) COMPUTER-AIDED METHOD FOR FRACTURE REDUCTION, AND ELECTRONIC DEVICE

(71) Applicant: BOE Technology Group Co., Ltd., Beijing (CN)

(72) Inventor: Hao Wang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 0 days.

(21) Appl. No.: 17/433,219

(22) PCT Filed: Feb. 8, 2021

(86) PCT No.: PCT/CN2021/076008
§ 371 (c)(1),
(2) Date: Aug. 23, 2021

(87) PCT Pub. No.: WO2021/164614
PCT Pub. Date: Aug. 26, 2021

(65) Prior Publication Data
US 2023/0136765 A1     May 4, 2023

(30) Foreign Application Priority Data

Feb. 19, 2020   (CN) .......................... 202010102288.9

(51) Int. Cl.
*A61B 34/10*     (2016.01)
*A61B 6/00*     (2006.01)
(Continued)

(52) U.S. Cl.
CPC ............ *A61B 34/10* (2016.02); *A61B 6/4441* (2013.01); *A61B 6/505* (2013.01); *G06T 7/0012* (2013.01);
(Continued)

(58) Field of Classification Search
None
See application file for complete search history.

(56) References Cited

U.S. PATENT DOCUMENTS 10,258,377 B1 *   4/2019   Lavi ....................... A61B 34/10
2004/0068187 A1   4/2004   Krause et al.

FOREIGN PATENT DOCUMENTS

CN     103750888 A     4/2014
CN     107550567 A     1/2018
(Continued)

OTHER PUBLICATIONS

Research and Development of Bone External Fixation System.
(Continued)

*Primary Examiner* — Leon Flores
(74) *Attorney, Agent, or Firm* — IPro, PLLC

(57) ABSTRACT

Provided are a computer-aided method and apparatus for fracture reduction, and an electronic device. The method includes: acquiring an anteroposterior image and a lateral image of a fracture site in process 101, wherein the anteroposterior image includes an anteroposterior image of a first bone (22) and an anteroposterior image of a second bone (24), and the lateral image includes a lateral image of the first bone (22) and a lateral image of the second bone (24); determining a vector of an axis of the first bone (22) in space based on the anteroposterior image of the first bone (22) and the lateral image of the first bone (22), and determining a vector of an axis of the second bone (24) in space based on the anteroposterior image of the second bone (24) and the lateral image of the second bone (24) in process 102; and determining an included angle between the first bone and the second bone in the spatial coordinate system based on the
(Continued)

vector of the axis (222) of the first bone (22) in space and the vector of the axis (242) of the second bone (24) in space in process 103.

17 Claims, 7 Drawing Sheets

(51) Int. Cl.
*A61B 6/50* (2024.01)
*G06T 7/00* (2017.01)
*G06T 7/73* (2017.01)
*G16H 30/40* (2018.01)
*G16H 50/20* (2018.01)

(52) U.S. Cl.
CPC .................. *G06T 7/73* (2017.01); *G06T 7/97* (2017.01); *G16H 30/40* (2018.01); *G16H 50/20* (2018.01); *G06T 2207/10116* (2013.01); *G06T 2207/30008* (2013.01)

(56) References Cited

FOREIGN PATENT DOCUMENTS

| CN | 111276244 A | 6/2020 |
|----|-------------|--------|
| WO | 2014048447 A1 | 4/2014 |

OTHER PUBLICATIONS

Plate prebending for long bone fracture based on pre-registration of fractured bone axial line.
Research on the Long Bone Skeleton 3D Reconstruction Method Based on Biplanar Orthogonal X-Ray Views.

* cited by examiner

| Acquiring an anteroposterior image and a lateral image of a fracture site, wherein the anteroposterior image includes an anteroposterior image of a first bone and an anteroposterior image of a second bone, and the lateral image includes a lateral image of the first bone and a lateral image of the second bone | 101 |

| Determining a vector of an axis of the first bone in a spatial coordinate system based on the anteroposterior image of the first bone and the lateral image of the first bone, and determining a vector of an axis of the second bone in the spatial coordinate system based on the anteroposterior image of the second bone and the lateral image of the second bone | 102 |

| Determining an included angle between the first bone and the second bone in space based on the vector of the axis of the first bone in the spatial coordinate system and the vector of the axis of the second bone in the spatial coordinate system | 103 |

FIG. 1

```
┌─────────────────────────────────────────────────────────────────────┐
│ Acquiring an anteroposterior image and a lateral image of a fracture site, wherein the │──201
│   anteroposterior image includes an anteroposterior image of a first bone and an       │
│   anteroposterior image of a second bone, and the lateral image includes a lateral     │
│        image of the first bone and a lateral image of the second bone                  │
└─────────────────────────────────────────────────────────────────────┘
                                    ↓
┌─────────────────────────────────────────────────────────────────────┐
│   Acquiring an anteroposterior boundary region of the first bone based on the          │──202
│  anteroposterior image of the first bone, and acquiring a lateral boundary region of   │
│      the first bone based on the lateral image of the first bone; and acquiring an     │
│  anteroposterior boundary region of the second bone based on anteroposterior image     │
│ of the second bone, and acquiring a lateral boundary region of the second bone based   │
│                      on the lateral image of the second bone                           │
└─────────────────────────────────────────────────────────────────────┘
                                    ↓
┌─────────────────────────────────────────────────────────────────────┐
│   Selecting an anteroposterior fracture boundary region of the first bone from the     │
│    anteroposterior boundary region of the first bone, and selecting a lateral fracture │──203
│ boundary region of the first bone from the lateral boundary region of the first bone;  │
│  and selecting an anteroposterior fracture boundary region of the second bone from     │
│     the anteroposterior boundary region of the second bone, and selecting a lateral    │
│ fracture boundary region of the second bone from the lateral boundary region of the    │
│                                    second bone                                         │
└─────────────────────────────────────────────────────────────────────┘
                                    ↓
┌─────────────────────────────────────────────────────────────────────┐
│   Acquiring coordinate values of a plurality of pixel points in the anteroposterior    │──204
│      fracture boundary region of the first bone, and acquiring coordinate values of a  │
│  plurality of pixel points in the lateral fracture boundary region of the first bone; and │
│     acquiring coordinate values of a plurality of pixel points in the anteroposterior  │
│     fracture boundary region of the second bone, and acquiring coordinate values of a  │
│   plurality of pixel points in the lateral fracture boundary region of the second bone │
└─────────────────────────────────────────────────────────────────────┘
                                    ↓                                        ──205
┌─────────────────────────────────────────────────────────────────────┐
│  Acquiring an anteroposterior axis equation of the first bone, and acquiring a lateral │
│  axis equation of the first bone; and acquiring an anteroposterior axis equation of the│
│        second bone, and acquiring a lateral axis equation of the second bone           │
└─────────────────────────────────────────────────────────────────────┘
                                    ↓
┌─────────────────────────────────────────────────────────────────────┐
│ Calculating an actual equation of the anteroposterior axis of the first bone through a │
│ least squares algorithm based on the coordinate values of the plurality of pixel points│
│    in the anteroposterior fracture boundary region of the first bone and the acquired  │
│   anteroposterior axis equation of the first bone, and calculating an actual equation of│
│     the lateral axis of the first bone through the least squares algorithm based on the│
│     coordinate values of the plurality of pixel points in the lateral fracture boundary│
│       region of the first bone and the acquired lateral axis equation of the first bone; and │──206
│ calculating an actual equation of the anteroposterior axis of the second bone through  │
│   the least squares algorithm based on the coordinate values of the plurality of pixel │
│    points in the anteroposterior fracture boundary region of the second bone and the   │
│  acquired anteroposterior axis equation of the second bone, and calculating an actual  │
│   equation of the lateral axis of the second bone through the least squares algorithm  │
│    based on the coordinate values of the plurality of pixel points in the lateral fracture│
│      boundary region of the second bone and the acquired lateral axis equation of the  │
│                                    second bone                                         │
└─────────────────────────────────────────────────────────────────────┘
```

FIG. 2A

COMPUTER-AIDED METHOD FOR FRACTURE REDUCTION, AND ELECTRONIC DEVICE

CROSS REFERENCE TO RELATED APPLICATION

This application is a US national stage of international application No. PCT/CN2021/076008, filed on Feb. 8, 2021, which claims priority to Chinese Patent Application No. 202010102288.9, filed on Feb. 19, 2020 and entitled "COMPUTER-AIDED METHOD FOR FRACTURE REDUCTION," the disclosure of which are herein incorporated by reference in their entireties.

TECHNICAL FIELD

The present disclosure relates to a computer-aided method and apparatus for fracture reduction, and an electronic device.

BACKGROUND

Reduction of severe fracture is usually carried out by using built-in steel nails. It is required to firstly align fracture sites before steel nails are fixed. However, evaluation criteria for bone alignment often rely on experience of a doctor, sometimes bones are not aligned well, which is found until postoperative recovery is completed, and thus, the bones are unable to recover, which causes physical and psychological effects on a patient. Therefore, it is very important to ensure the bone alignment.

SUMMARY

Embodiments of the present disclosure provide a computer-aided method and apparatus for fracture reduction, and an electronic device.

At least one embodiment of the present disclosure provides a computer-aided method for fracture reduction. The method includes:
acquiring an anteroposterior image and a lateral image of a fracture site, wherein the anteroposterior image includes an anteroposterior image of a first bone and an anteroposterior image of a second bone, and the lateral image includes a lateral image of the first bone and a lateral image of the second bone, the first bone and the second bone being two bones at the fracture site;
  determining a vector of an axis of the first bone in space based on the anteroposterior image and the lateral image of the first bone, and determining a vector of an axis of the second bone in space based on the anteroposterior image of the second bone and the lateral image of the second bone; and
  determining an included angle between the first bone and the second bone in the spatial coordinate system based on the vector of the axis of the first bone in spatial coordinate system and the vector of the axis of the second bone in spatial coordinate system, wherein the included angle is configured to indicate a direction of fracture reduction.

Optionally, determining the vector of the axis of the first bone in the spatial coordinate system based on the anteroposterior image of the first bone and the lateral image of the first bone, and determining the vector of the axis of the second bone in the spatial coordinate system based on the anteroposterior image of the second bone and the lateral image of the second bone include:
  acquiring an actual equation of an anteroposterior axis of the first bone based on the anteroposterior image of the first bone, and acquiring an actual equation of a lateral axis of the first bone based on the lateral image of the first bone; and acquiring an actual equation of an anteroposterior axis of the second bone based on the anteroposterior image of the second bone, and acquiring an actual equation of a lateral axis of the second bone based on the lateral image of the second bone; and
  determining the vector of the axis of the first bone in the spatial coordinate system based on the actual equation of the anteroposterior axis of the first bone and the actual equation of the lateral axis of the first bone; and determining the vector of the axis of the second bone in the spatial coordinate system based on the actual equation of the anteroposterior axis of the second bone and the actual equation of the lateral axis of the second bone.

Optionally, acquiring the actual equation of the anteroposterior axis of the first bone based on the anteroposterior image of the first bone, and acquiring the actual equation of the lateral axis of the first bone based on the lateral image of the first bone; and acquiring the actual equation of the anteroposterior axis of the second bone based on the anteroposterior image of the second bone, and acquiring the actual equation of the lateral axis of the second bone based on the lateral image of the second bone include:
  acquiring coordinate values of a plurality of pixel points in an anteroposterior fracture boundary region of the first bone based on the anteroposterior image of the first bone, and acquiring coordinate values of a plurality of pixel points in a lateral fracture boundary region of the first bone based on the lateral image of the first bone; and acquiring coordinate values of a plurality of pixel points in an anteroposterior fracture boundary region of the second bone based on the anteroposterior image of the second bone, and acquiring coordinate values of a plurality of pixel points in a lateral fracture boundary region of the second bone based on the lateral image of the second bone; and
  calculating the actual equation of the anteroposterior axis of the first bone based on the coordinate values of the plurality of pixel points in the anteroposterior fracture boundary region of the first bone, and calculating the actual equation of the lateral axis of the first bone based on the coordinate values of the plurality of pixel points in the lateral fracture boundary region of the first bone; and calculating the actual equation of the anteroposterior axis of the second bone based on the coordinate values of the plurality of pixel points in the anteroposterior fracture boundary region of the second bone, and calculating the actual equation of the lateral axis of the second bone based on the coordinate values of the plurality of pixel points in the lateral fracture boundary region of the second bone.

Optionally, acquiring the coordinate values of the plurality of pixel points in the anteroposterior fracture boundary region of the first bone based on the anteroposterior image of the first bone, and acquiring the coordinate values of the plurality of pixel points in the lateral fracture boundary region of the first bone based on the lateral image of the first bone; and acquiring the coordinate values of the plurality of pixel points in the anteroposterior fracture boundary region of the second bone based on the anteroposterior image of the second bone, and acquiring the coordinate values of the plurality of pixel points in the lateral fracture boundary region of the second bone based on the lateral image of the second bone include:

acquiring the anteroposterior fracture boundary region of the first bone based on the anteroposterior image of the first bone, and acquiring the lateral fracture boundary region of the first bone based on the lateral image of the first bone; and acquiring the anteroposterior fracture boundary region of the second bone based on the anteroposterior image of the second bone, and acquiring the lateral fracture boundary region of the second bone based on the lateral image of the second bone; and acquiring the coordinate values of the plurality of pixel points in the anteroposterior fracture boundary region of the first bone, and acquiring the coordinate values of the plurality of pixel points in the lateral fracture boundary region of the first bone; and acquiring the coordinate values of the plurality of pixel points in the anteroposterior fracture boundary region of the second bone, and acquiring the coordinate values of the plurality of pixel points in the lateral fracture boundary region of the second bone.

Optionally, acquiring the anteroposterior fracture boundary region of the first bone based on the anteroposterior image of the first bone, and acquiring the lateral fracture boundary region of the first bone based on the lateral image of the first bone; and acquiring the anteroposterior fracture boundary region of the second bone based on the anteroposterior image of the second bone, and acquiring the lateral fracture boundary region of the second bone based on the lateral image of the second bone include:

acquiring an anteroposterior boundary region of the first bone based on the anteroposterior image of the first bone, and acquiring a lateral boundary region of the first bone based on the lateral image of the first bone; and acquiring an anteroposterior boundary region of the second bone based on the anteroposterior image of the second bone, and acquiring a lateral boundary region of the second bone based on the lateral image of the second bone; and selecting the anteroposterior fracture boundary region of the first bone from the anteroposterior boundary region of the first bone, and selecting the lateral fracture boundary region of the first bone from the lateral boundary region of the first bone; and selecting the anteroposterior fracture boundary region of the second bone from the anteroposterior boundary region of the second bone, and selecting the lateral fracture boundary region of the second bone from the lateral boundary region of the second bone.

Optionally, calculating the actual equation of the anteroposterior axis of the first bone based on the coordinate values of the plurality of pixel points in the anteroposterior fracture boundary region of the first bone, and calculating the actual equation of the lateral axis of the first bone based on the coordinate values of the plurality of pixel points in the lateral fracture boundary region of the first bone; and calculating the actual equation of the anteroposterior axis of the second bone based on the coordinate values of the plurality of pixel points in the anteroposterior fracture boundary region of the second bone, and calculating the actual equation of the lateral axis of the second bone based on the coordinate values of the plurality of pixel points in the lateral fracture boundary region of the second bone include:

acquiring an anteroposterior axis equation of the first bone, and acquiring a lateral axis equation of the first bone; and acquiring an anteroposterior axis equation of the second bone, and acquiring a lateral axis equation of the second bone; and calculating the actual equation of the anteroposterior axis of the first bone through a least squares algorithm based on the coordinate values of the plurality of pixel points in the anteroposterior fracture boundary region of the first bone and the acquired anteroposterior axis equation of the first bone, and calculating the actual equation of the lateral axis of the first bone through the least squares algorithm based on the coordinate values of the plurality of pixel points in the lateral fracture boundary region of the first bone and the acquired lateral axis equation of the first bone; and calculating the actual equation of the anteroposterior axis of the second bone through the least squares algorithm based on the coordinate values of the plurality of pixel points in the anteroposterior fracture boundary region of the second bone and the acquired anteroposterior axis equation of the second bone, and calculating the actual equation of the lateral axis of the second bone through the least squares algorithm based on the coordinate values of the plurality of pixel points in the lateral fracture boundary region of the second bone and the acquired lateral axis equation of the second bone.

Optionally, a plane in which the anteroposterior image of the first bone and the anteroposterior image of the second bone are disposed is an XOZ plane, and a plane in which the lateral image of the first bone and the lateral image of the second bone are disposed is a YOZ plane; and determining the vector of the axis of the first bone in the spatial coordinate system based on the actual equation of the anteroposterior axis of the first bone and the actual equation of the lateral axis of the first bone, and determining the vector of the axis of the second bone in the spatial coordinate system based on the actual equation of the anteroposterior axis of the second bone and the actual equation of the lateral axis of the second bone include:

acquiring a vector of the anteroposterior axis of the first bone in the XOZ plane based on the actual equation of the anteroposterior axis of the first bone, and acquiring a vector of the lateral axis of the first bone in the YOZ plane based on the actual equation of the lateral axis of the first bone; and acquiring a vector of the anteroposterior axis of the second bone in the XOZ plane based on the actual equation of the anteroposterior axis of the second bone, and acquiring a vector of the lateral axis of the second bone in the YOZ plane based on the actual equation of the lateral axis of the second bone;

selecting a first specific point on the axis of the first bone, and acquiring coordinate values of the first specific point on the anteroposterior axis of the first bone in the XOZ plane and coordinate values of the first specific point on the lateral axis of the first bone in the YOZ plane; and selecting a second specific point on the axis of the second bone, and acquiring coordinate values of the second specific point on the anteroposterior axis of the second bone in the XOZ plane and coordinate values of the second specific point on the lateral axis of the second bone in the YOZ plane; and acquiring the vector of the axis of the first bone in the spatial coordinate system based on the coordinate values of the first specific point of the first bone on the anteroposterior axis in the XOZ plane, the vector of the anteroposterior axis of the first bone in the XOZ plane, the coordinate values of the first specific point of the first bone on the lateral axis in the YOZ plane and the vector of the lateral axis of the first bone in the YOZ plane; and acquiring the vector of the axis of the second bone in the spatial coordinate system based on the coordinate values of the second specific point of the second bone on the anteroposterior axis in the XOZ plane, the vector of the anteroposterior axis of the second bone in the XOZ plane, the coordinate values of the second specific point of the second bone on the lateral axis in the YOZ plane and the vector of the lateral axis of the second bone in the YOZ plane.

At least one embodiment of the present disclosure provides a computer-aided apparatus for fracture reduction. The apparatus includes:

an acquiring module, configured to acquire an anteroposterior image and a lateral image of a fracture site, wherein the anteroposterior image includes an anteroposterior image of a first bone and an anteroposterior image of a second bone, and the lateral image includes a lateral image of the first bone and a lateral image of the second bone, the first bone and the second bone being two bones at the fracture site;

a first determining module, configured to determine a vector of an axis of the first bone in a spatial coordinate system based on the anteroposterior image of the first bone and the lateral image of the first bone, and determine a vector of an axis of the second bone in the spatial coordinate system based on the anteroposterior image of the second bone and the lateral image of the second bone; and a second determining module, configured to determine an included angle between the first bone and the second bone in the spatial coordinate system based on the vector of the axis of the first bone in the spatial coordinate system and the vector of the axis of the second bone in the spatial coordinate system, wherein the included angle is configured to indicate a direction of fracture reduction.

Optionally, the first determining module includes:

a first determining unit, configured to acquire an actual equation of an anteroposterior axis of the first bone based on the anteroposterior image of the first bone, and acquire an actual equation of a lateral axis of the first bone based on the lateral image of the first bone; and determine the vector of the axis of the first bone in the spatial coordinate system based on the actual equation of the anteroposterior axis of the first bone and the actual equation of the lateral axis of the first bone; and a second determining unit, configured to acquire an actual equation of an anteroposterior axis of the second bone based on the anteroposterior image of the second bone, and acquire an actual equation of a lateral axis of the second bone based on the lateral image of the second bone; and determine the vector of the axis of the second bone in the spatial coordinate system based on the actual equation of the anteroposterior axis of the second bone and the actual equation of the lateral axis of the second bone.

Optionally, the first determining unit is configured to acquire coordinate values of a plurality of pixel points in an anteroposterior fracture boundary region of the first bone based on the anteroposterior image of the first bone, and acquire coordinate values of a plurality of pixel points in a lateral fracture boundary region of the first bone based on the lateral image of the first bone; and calculate the actual equation of the anteroposterior axis of the first bone based on the coordinate values of the plurality of pixel points in the anteroposterior fracture boundary region of the first bone, and calculate the actual equation of the lateral axis of the first bone based on the coordinate values of the plurality of pixel points in the lateral fracture boundary region of the first bone; and the second determining unit is configured to acquire coordinate values of a plurality of pixel points in an anteroposterior fracture boundary region of the second bone based on the anteroposterior image of the second bone, and acquire coordinate values of a plurality of pixel points in a lateral fracture boundary region of the second bone based on the lateral image of the second bone; and calculate the actual equation of the anteroposterior axis of the second bone based on the coordinate values of the plurality of pixel points in the anteroposterior fracture boundary region of the second bone, and calculate the actual equation of the lateral axis of the second bone based on the coordinate values of the plurality of pixel points in the lateral fracture boundary region of the second bone.

Optionally, the first determining unit is configured to acquire the anteroposterior fracture boundary region of the first bone based on the anteroposterior image of the first bone, and acquire the lateral fracture boundary region of the first bone based on the lateral image of the first bone; and acquire coordinate values of the plurality of pixel points in the anteroposterior fracture boundary region of the first bone, and acquire coordinate values of the plurality of pixel points in the lateral fracture boundary region of the first bone; and the second determining unit is configured to acquire the anteroposterior fracture boundary region of the second bone based on the anteroposterior image of the second bone, and acquire the lateral fracture boundary region of the second bone based on the lateral image of the second bone; and acquire coordinate values of the plurality of pixel points of the anteroposterior fracture boundary region of the second bone, and acquire coordinate values of the plurality of pixel points of the lateral fracture boundary region of the second bone.

Optionally, the first determining unit is configured to acquire an anteroposterior boundary region of the first bone based on the anteroposterior image of the first bone, and acquire a lateral boundary region of the first bone based on the lateral image of the first bone; and select the anteroposterior fracture boundary region of the first bone from the anteroposterior boundary region of the first bone, and select the lateral fracture boundary region of the first bone from the lateral boundary region of the first bone; and the second determining unit is configured to acquire an anteroposterior boundary region of the second bone based on the anteroposterior image of the second bone, and acquire a lateral boundary region of the second bone based on the lateral image of the second bone; and select the anteroposterior fracture boundary region of the second bone from the anteroposterior boundary region of the second bone, and select the lateral fracture boundary region of the second bone from the lateral boundary region of the second bone.

Optionally, the first determining unit is configured to acquire an anteroposterior axis equation of the first bone, and acquire a lateral axis equation of the first bone; and calculate the actual equation of the anteroposterior axis of the first bone through a least squares algorithm based on the coordinate values of the plurality of pixel points in the anteroposterior fracture boundary region of the first bone and the acquired anteroposterior axis equation of the first bone, and calculate the actual equation of the lateral axis of the first bone through the least squares algorithm based on the coordinate values of the plurality of pixel points in the lateral fracture boundary region of the first bone and the acquired lateral axis equation of the first bone; and the second determining unit is configured to acquire an anteroposterior axis equation of the second bone, and acquire a lateral axis equation of the second bone; and calculate the actual equation of the anteroposterior axis of the second bone through the least squares algorithm based on the coordinate values of the plurality of pixel points in the anteroposterior fracture boundary region of the second bone and the acquired anteroposterior axis equation of the second bone, and calculate the actual equation of the lateral axis of the second bone through the least squares algorithm based on the coordinate values of the plurality of pixel points in the lateral fracture boundary region of the second bone and the acquired lateral axis equation of the second bone.

Optionally, a plane in which the anteroposterior image of the first bone and the anteroposterior image of the second bone are disposed is an XOZ plane, and a plane in which the lateral image of the first bone and the lateral image of the second bone are disposed is a YOZ plane;

the first determining unit is configured to acquire a vector of the anteroposterior axis of the first bone in the XOZ plane based on the actual equation of the anteroposterior axis of the first bone, and acquire a vector of the lateral axis of the first bone in the YOZ plane based on the actual equation of the lateral axis of the first bone; select a first specific point on the axis of the first bone, and acquire coordinate values of the first specific point on the anteroposterior axis of the first bone in the XOZ plane and coordinate values of the first specific point on the lateral axis of the first bone in the YOZ plane; and acquire the vector of the axis of the first bone in the spatial coordinate system based on the coordinate values of the first specific point of the first bone on the anteroposterior axis in the XOZ plane, the vector of the anteroposterior axis of the first bone in the XOZ plane, the coordinate values of the first specific point of the first bone on the lateral axis in the YOZ plane and the vector of the lateral axis of the first bone in the YOZ plane; and the second determining unit is configured to acquire a vector of the anteroposterior axis of the second bone in the XOZ plane based on the actual equation of the anteroposterior axis of the second bone, and acquire a vector of the lateral axis of the second bone in the YOZ plane based on the actual equation of the lateral axis of the second bone; select a second specific point on the axis of the second bone, and acquire coordinate values of the second specific point on the anteroposterior axis of the second bone in the XOZ plane and coordinate values of the second specific point on the lateral axis of the second bone in the YOZ plane; and acquire the vector of the axis of the second bone in the spatial coordinate system based on the coordinate values of the second specific point of the second bone on the anteroposterior axis in the XOZ plane, the vector of the anteroposterior axis of the second bone in the XOZ plane, the coordinate values of the second specific point of the second bone on the lateral axis in the YOZ plane and the vector of the lateral axis of the second bone in the YOZ plane.

At least one embodiment of the present disclosure further provides an electronic device. The device includes:

a memory storing at least one program code therein and a processor, wherein the program code, when loaded and executed by the processor, causes the processor to perform the computer-aided method for fracture reduction.

At least one embodiment of the present disclosure further provides a non-transitory storage medium storing at least one program code therein, wherein the program code, when loaded and executed by a processor, causes the processor to perform the computer-aided method for fracture reduction.

At least one embodiment of the present disclosure further provides a G-arm X-ray device. The device includes a front-view X-ray portion, a side-view X-ray portion and a controller;

wherein the front-view X-ray portion is configured to capture an anteroposterior image of a fracture site, and the side-view X-ray portion is configured to capture a lateral image of the fracture site, the anteroposterior image and the lateral image being transmitted to the controller; the controller is configured to perform the computer-aided method for fracture reduction.

BRIEF DESCRIPTION OF THE DRAWINGS

FIG. 1 is a flowchart of a computer-aided method for fracture reduction according to an embodiment of the present disclosure;

Figure 3:
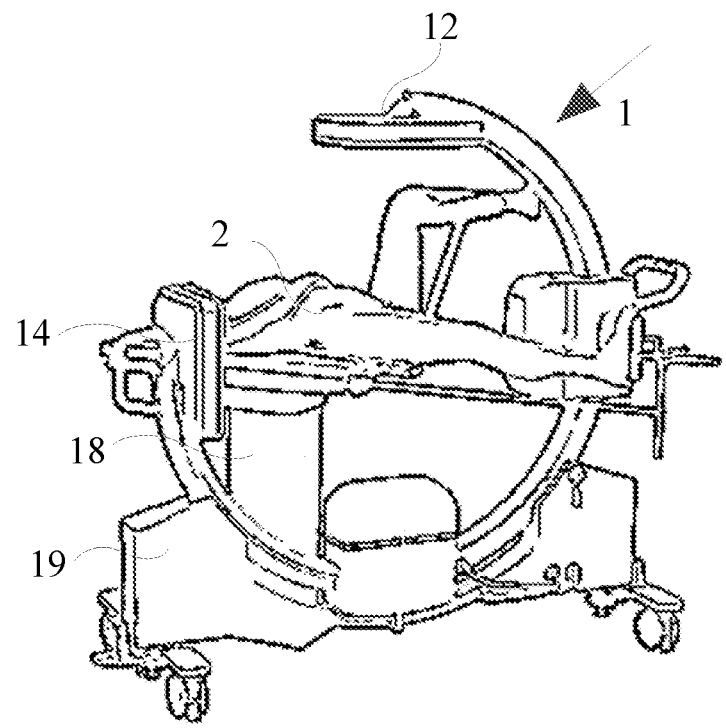
Figure 4:
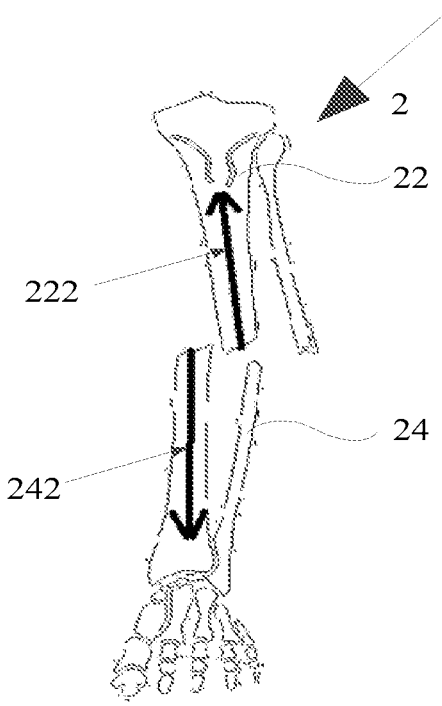
Figure 5:
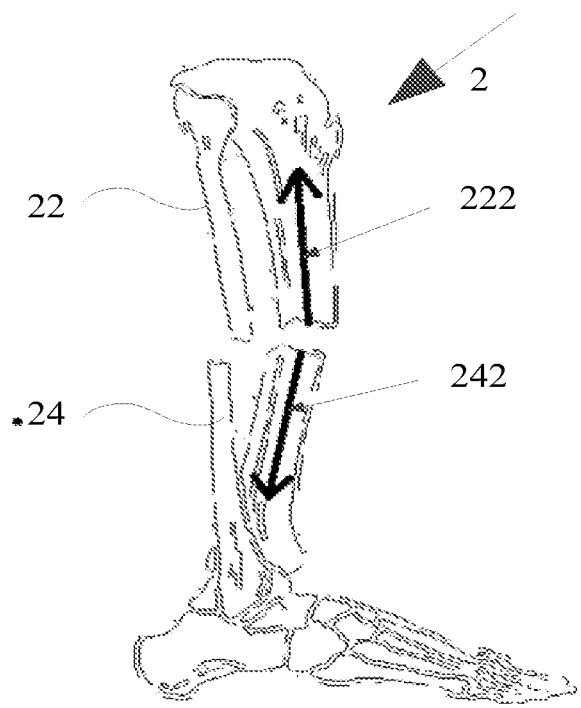
Figure 6:
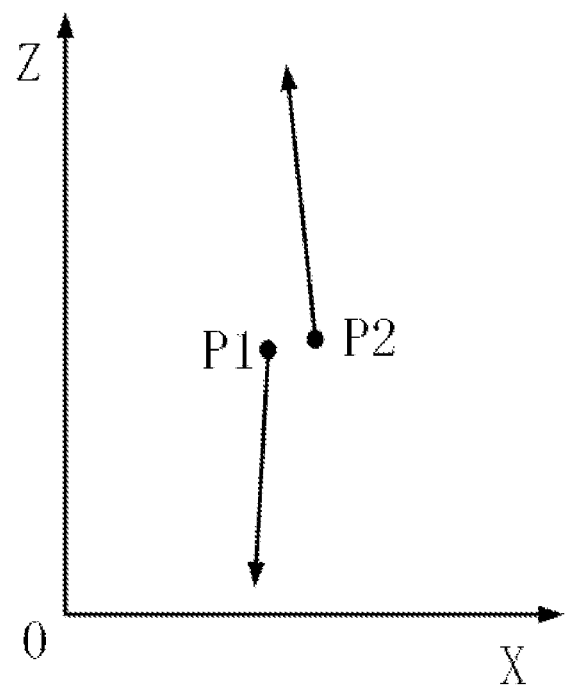
Figure 7:
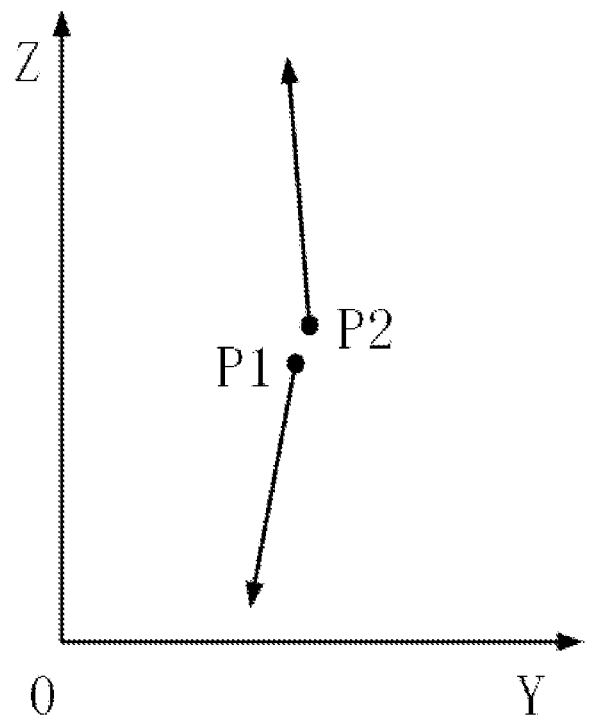
Figure 8:
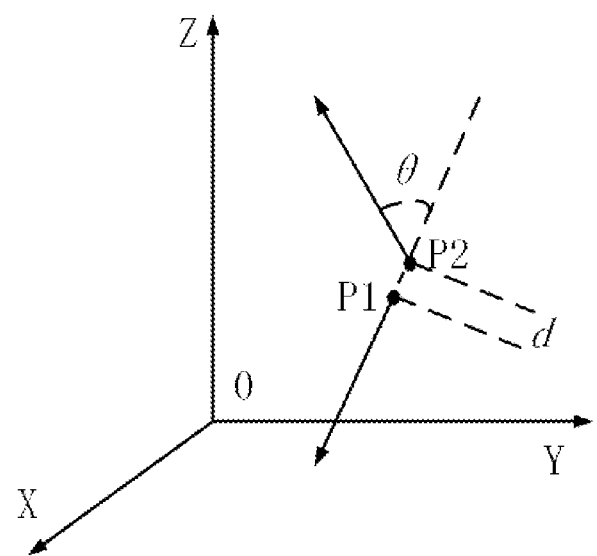
Figure 9:
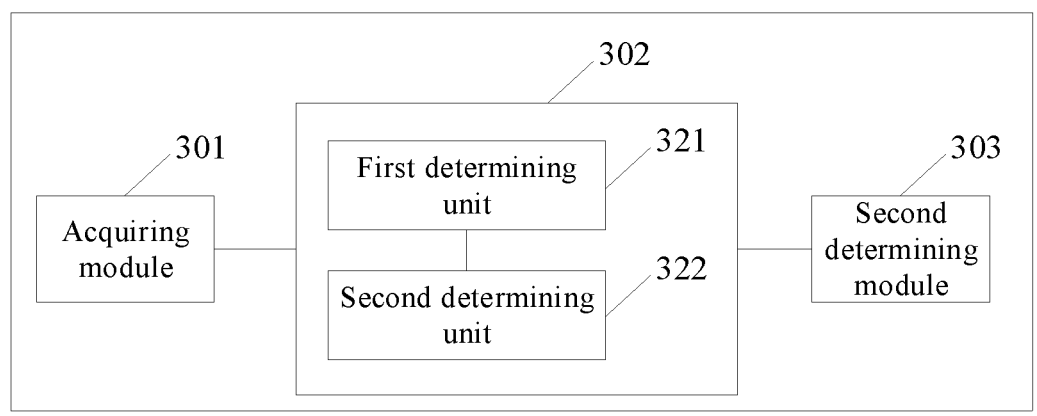
Figure 10:
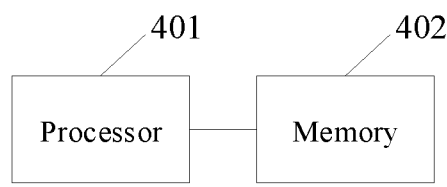

2B is a second part of the flowchart of another computer-aided method for fracture reduction according to an embodiment of the present disclosure;

FIG. 3 is a structural schematic diagram of a G-arm X-ray device according to an embodiment of the present disclosure;

FIG. 4 illustrates an anteroposterior image of a fracture site according to an embodiment of the present disclosure;

FIG. 5 illustrates a lateral image of a fracture site according to an embodiment of the present disclosure;

FIG. 6 is a schematic diagram of an anteroposterior axis of a first bone and an anteroposterior axis of a second bone in a plane coordinate system according to an embodiment of the present disclosure;

FIG. 7 is a schematic diagram of a lateral axis of a first bone and a lateral axis of a second bone in a plane coordinate system according to an embodiment of the present disclosure;

FIG. 8 is a schematic diagram of an axis of a first bone and an axis of a second bone in a spatial coordinate system according to an embodiment of the present disclosure;

FIG. 9 is a structural schematic diagram of a computer-aided apparatus for fracture reduction according to an embodiment of the present disclosure; and FIG. 10 is a structural block diagram of an electronic device according to an embodiment of the present disclosure.

REFERENCE NUMERALS AND DENOTATIONS THEREOF

1—G-arm X-ray device, 12—front-view X-ray portion, 14—side-view X-ray portion, 18—movable table, 2—fracture site, 22—first bone, 222—axis of first bone, 24—second bone, 242—axis of second bone, 301—acquiring module, 302—first determining module, 303—second determining module, 321—first determining unit, 322—second determining unit, 401—processor, and 402—memory.

DETAILED DESCRIPTION

In order to further illustrate the technical solutions adopted by the present disclosure for achieving the predetermined objectives and effects thereof, specific implementations, structures, features and effects of a computer-aided method for fracture reduction according to the present disclosure are described in detail hereinafter with reference to the accompanying drawings and embodiments.

In the related art, a G-arm is generally used to capture an anteroposterior image and a lateral image of a fracture site. The reduction is usually carried out in two steps. That is, the bones are firstly aligned in one of anteroposterior direction and lateral direction, and then aligned in another direction based on the anteroposterior image and the lateral image. The reduction is carried out in two steps, therefore a secondary fracture may occur.

Therefore, it becomes an urgent problem to be solved to provide a method for directly acquiring a direction of fracture reduction.

As shown in FIG. 1 to FIG. 8, an embodiment of the present disclosure provides a computer-aided method for fracture reduction. The method includes the following processes.

In 101, an anteroposterior image and a lateral image of a fracture site are acquired, wherein the anteroposterior image includes an anteroposterior image of a first bone and an anteroposterior image of a second bone, and the lateral image includes a lateral image of the first bone and a lateral image of the second bone, the first bone and the second bone being two bones at the fracture site.

As shown in FIG. 3, a fracture site 2 of a patient is anesthetized and mechanically fixed, and then placed under a G-arm X-ray device 1 to acquire anteroposterior and lateral images of the fracture site 2 by capturing. After the images are captured, the fracture site 2 is not moved, so as to avoid re-capturing.

There is a 90 degree difference between the capture angle of the anteroposterior image and the lateral image. For example, the anteroposterior image is an image captured from a front side of a human body, and the lateral image is an image captured from a lateral side of the human body.

In 102, a vector of an axis of the first bone in a spatial coordinate system is determined based on the anteroposterior image of the first bone and the lateral image of the first bone, and a vector of an axis of the second bone in the spatial coordinate system is determined based on the anteroposterior image of the second bone and the lateral image of the second bone.

In 103, an included angle between the first bone and the second bone in space is determined based on the vector of the axis of the first bone in the spatial coordinate system and the vector of the axis of the second bone in the spatial coordinate system.

As shown in FIG. 1 and FIG. 4 to FIG. 8, a computer-aided method for fracture reduction according to an embodiment of the present disclosure includes: acquiring an anteroposterior image and a lateral image of a fracture site 2. In a severe fracture, the fracture refers to two bones that have certain angular deviation; wherein the fracture site includes a first bone 22 and a second bone 24, the anteroposterior image includes an anteroposterior image of the first bone 22 and an anteroposterior image of the second bone 24, and the lateral image includes a lateral image of the first bone 22 and a lateral image of the second bone 24. The method further includes: determining a vector of an axis 222 of the first bone 22 in the spatial coordinate system based on the anteroposterior image of the first bone 22 and the lateral image of the first bone 22, and determining a vector of an axis 242 of the second bone 24 in the spatial coordinate system based on the anteroposterior image of the second bone 24 and the lateral image of the second bone 24, and thereby acquiring vectors of the axis 222 of the first bone 22 and the axis 242 of the second bone 24 in the spatial coordinate system. The method further includes: determining an included angle between the axis 222 of the first bone 22 and the axis 242 of the second bone 24 in space based on the vectors of the axis 222 of the first bone 22 and the axis 242 of the second bone 24 in the spatial coordinate system. The included angle of the axes of two bones in space is the included angle of the first bone 22 and the second bone 24 in space; that is, the included angle of the first bone and the second bone in the spatial coordinate system is a rotation angle of the second bone 24 relative to the first bone 22. Thus, a direction of fracture reduction may be directly acquired based on the included angle of two bones, and a moving process may be directly performed based on the direction. Therefore, fracture reduction processes are simplified, a precision of bone alignment is improved, an operation effect is improved, and the occurrence of a secondary fracture is prevented.

Further, the included angle between the first bone and the second bone in the spatial coordinate system acquired by the method may not necessarily directly serve for treatment, which may also serve for guidance. For example, the included angle may guide a doctor to carry out fracture reduction, or provide guidance for comparison of reduction effects before and after treatment, or the like.

Figure 2B:
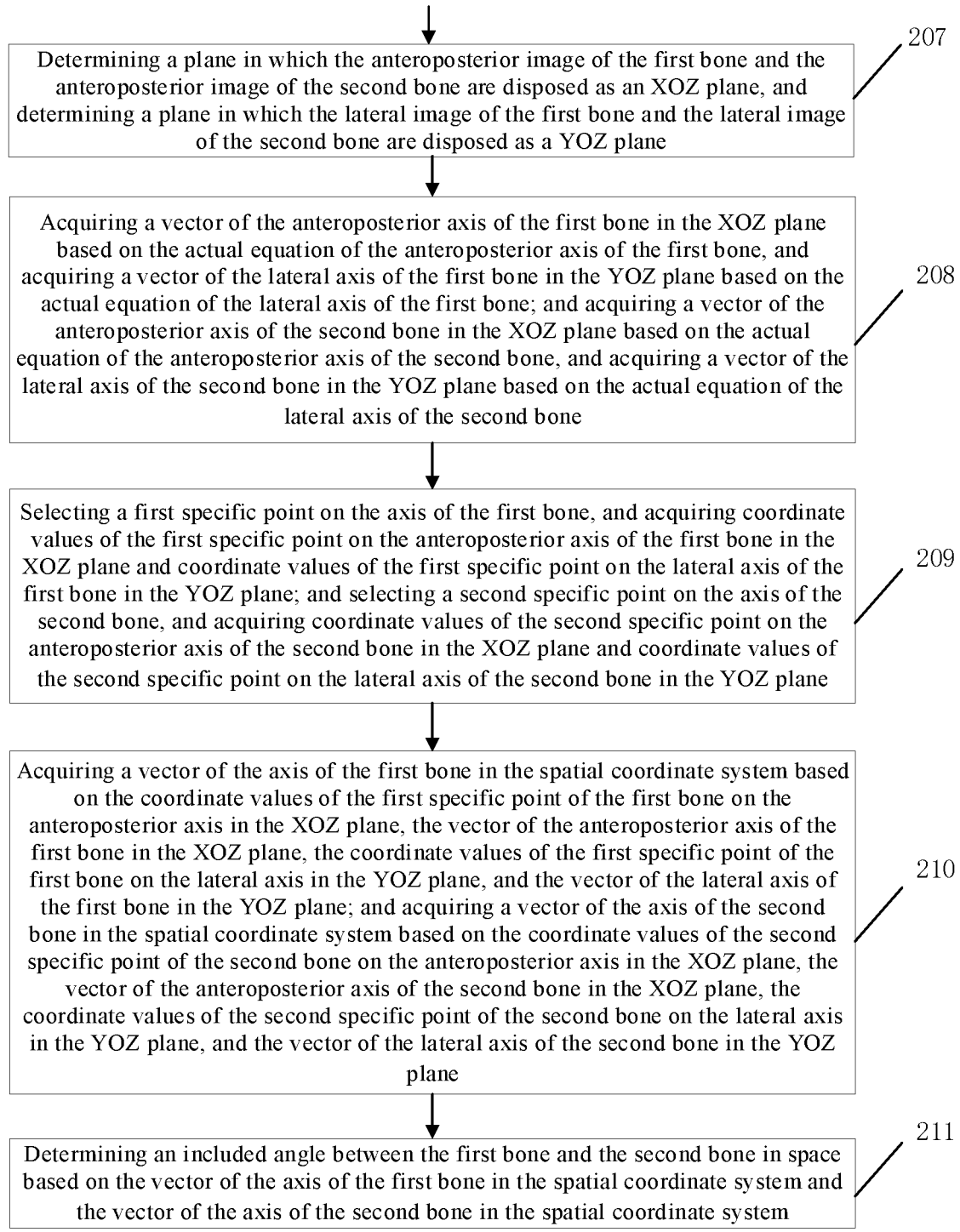
FIG. 2A is a first part of a flowchart of another computer-aided method for fracture reduction according to an embodiment of the present disclosure.

As shown in FIG. 2A and FIG. 2B, the present disclosure is further described in detail hereinafter with reference to the accompanying drawings and embodiments.

In 201, an anteroposterior image and a lateral image of a fracture site are acquired, wherein the anteroposterior image includes an anteroposterior image of a first bone and an anteroposterior image of a second bone, and the lateral image includes a lateral image of the first bone and a lateral image of the second bone.

In 202, an anteroposterior boundary region of the first bone is acquired based on the anteroposterior image of the first bone, and a lateral boundary region of the first bone is acquired based on the lateral image of the first bone; and an anteroposterior boundary region of the second bone is acquired based on the anteroposterior image of the second bone, and a lateral boundary region of the second bone is acquired based on the lateral image of the second bone.

As shown in FIG. 4 and FIG. 5, in this embodiment, a region where two bones at the fracture site 2 are disposed is extracted by performing edge detection for the anteroposterior image of the first bone 22, the lateral image of the first bone 22, the anteroposterior image of the second bone 24 and the lateral image of the second bone 24 respectively using an image cutting algorithm, to acquire an anteroposterior boundary region of the first bone 22, a lateral boundary region of the first bone 22, an anteroposterior boundary region of the second bone 24 and a lateral boundary region of the second bone 24.

Optionally, the common image cutting algorithms include Sobel, Prewitt, Roberts and Canny, and the like.

In 203, an anteroposterior fracture boundary region of the first bone is selected from the anteroposterior boundary region of the first bone, and a lateral fracture boundary region of the first bone is selected from the lateral boundary region of the first bone; and an anteroposterior fracture boundary region of the second bone is selected from the anteroposterior boundary region of the second bone, and a lateral fracture boundary region of the second bone is selected from the lateral boundary region of the second bone.

In this embodiment, the anteroposterior fracture boundary region of the first bone 22, the lateral fracture boundary region of the first bone 22, the anteroposterior fracture boundary region of the second bone 24 and the lateral fracture boundary region of the second bone 24 are selected from the anteroposterior boundary region of the first bone 22, the lateral boundary region of the first bone 22, the anteroposterior boundary region of the second bone 24 and the lateral boundary region of the second bone 24 respectively. Generally, the fracture boundary region is determined based on sizes of areas. The connected region with the largest area in the anteroposterior and lateral boundary regions is the boundary region of the fracture. Therefore, the fracture boundary regions that best represent the first bone 22 and the second bone 24 are selected from the anteroposterior and lateral boundary regions of the first bone 22 and the second bone 24, which facilitates subsequent selection of the axis 222 of the first bone 22 and the axis 242 of the second bone 24.

In 204, coordinate values of a plurality of pixel points in the anteroposterior fracture boundary region of the first bone are acquired, and coordinate values of a plurality of pixel points in the lateral fracture boundary region of the first bone are acquired; and coordinate values of a plurality of pixel points in the anteroposterior fracture boundary region of the second bone are acquired, and coordinate values of a plurality of pixel points in the lateral fracture boundary region of the second bone are acquired.

As shown in FIG. 4 to FIG. 7, in this embodiment, when the anteroposterior and lateral images of the fracture are acquired, the image includes coordinate values of each pixel point; and the coordinate values of each pixel point in the anteroposterior fracture boundary region of the first bone 22 and the coordinate values of each pixel point in the lateral fracture boundary region of the first bone 22, and the coordinate values of each pixel point in the anteroposterior fracture boundary region of the second bone 24 and the coordinate values of each pixel point in the lateral fracture boundary region of the second bone 24 are selected from coordinate values of all pixel points. Taking the anteroposterior image of the first bone 22 as an example, the coordinates of each pixel point in the anteroposterior fracture boundary region of the first bone 22 are $(x_i, y_i)$.

In 205, an anteroposterior axis equation of the first bone is acquired, and a lateral axis equation of the first bone is acquired; and an anteroposterior axis equation of the second bone is acquired, and a lateral axis equation of the second bone is acquired.

In embodiments of the present disclosure, methods for acquiring an axis equation of a bone include but are not limited to: acquiring a manually input axis equation, acquiring a predetermined axis equation, or acquiring an axis equation based on a predetermined rule.

In this embodiment, the anteroposterior axis of the first bone is taken as an example. Firstly, the anteroposterior axis equation of the first bone is manually assumed as y=ax+b; and then, the axis equation is manually input into a device or preset in the device. At this time, the device may acquire the axis equation.

In 206, an actual equation of the anteroposterior axis of the first bone is calculated through a least squares algorithm based on the coordinate values of the plurality of pixel points in the anteroposterior fracture boundary region of the first bone and the acquired anteroposterior axis equation of the first bone, and an actual equation of the lateral axis of the first bone is calculated through the least squares algorithm based on the coordinate values of the plurality of pixel points in the lateral fracture boundary region of the first bone and the acquired lateral axis equation of the first bone; and an actual equation of the anteroposterior axis of the second bone is calculated through the least squares algorithm based on the coordinate values of the plurality of pixel points in the anteroposterior fracture boundary region of the second bone and the acquired anteroposterior axis equation of the second bone, and an actual equation of the lateral axis of the second bone is calculated through the least squares algorithm based on the coordinate values of the plurality of pixel points in the lateral fracture boundary region of the second bone and the acquired lateral axis equation of the second bone.

As shown in FIG. 4 to FIG. 7, in this embodiment, the actual equation of the anteroposterior axis of the first bone 22 is calculated as an example. The actual equation of the anteroposterior axis of the first bone 22 is calculated through the least squares algorithm. A sum of squares of distances from the coordinates $(x_i, y_i)$ of N pixel points in the anteroposterior fracture boundary region of the first bone 22 to the anteroposterior axis equation y=ax+b of the first bone 22 is acquired, wherein a distance from each pixel point to the anteroposterior axis of the first bone 22 is $d_i$, $$d_i = \frac{|ax_i + b - y_i|}{\sqrt{a^2 + (-1)^2}} = \frac{|ax_i - y_i + b|}{\sqrt{a^2 + 1}},$$

and the sum of squares of distances from the N pixel points in the anteroposterior fracture boundary region of the first bone 22 to the anteroposterior axis of the first bone 22 is $$\text{Sum} = \sum_{i=0}^{N} di^2.$$

Firstly, it is assumed that a=1 and b=1 initially, and then, the minimum value of the sum is acquired by iterative calculation to acquire values of a and b, thereby acquiring the actual equation of the anteroposterior axis of the first bone 22.

In this embodiment, when the axis of the first bone 22 and the axis of the second bone 24 are extracted by the above method, the doctor is required to determine the rationality of axis extraction, that is because the image algorithm relies on imaging quality of the image, in response to an exposure dose of the G-arm is insufficient, the captured image is very dark and may have some errors, and the image algorithm may be inaccurate at this time.

In 207, a plane in which the anteroposterior image of the first bone and the anteroposterior image of the second bone are disposed is determined as an XOZ plane, and a plane in which the lateral image of the first bone and the lateral image of the second bone are disposed is determined as a YOZ plane.

In 208, a vector of the anteroposterior axis of the first bone in the XOZ plane is acquired based on the actual equation of the anteroposterior axis of the first bone, and a vector of the lateral axis of the first bone in the YOZ plane is acquired based on the actual equation of the lateral axis of the first bone; and a vector of the anteroposterior axis of the second bone in the XOZ plane is acquired based on the actual equation of the anteroposterior axis of the second bone, and a vector of the lateral axis of the second bone in the YOZ plane is acquired based on the actual equation of the lateral axis of the second bone.

In this embodiment, the first bone 22 is taken as an example. The vector ($V_x$, $V_z$) of the anteroposterior axis in the XOZ plane is acquired based on the actual equation y=ax+b of the anteroposterior axis of the first bone 22; and similarly, the vector ($N_x$, $N_z$) of the lateral axis in the YOZ plane is acquired based on the actual equation of the lateral axis of the first bone 22.

In 209, a first specific point P1 is selected on the axis of the first bone, and coordinate values of the first specific point on the anteroposterior axis of the first bone in the XOZ plane and coordinate values of the first specific point on the lateral axis of the first bone in the YOZ plane are acquired; and a second specific point P2 is selected on the axis of the second bone, and coordinate values of the second specific point on the anteroposterior axis of the second bone in the XOZ plane and coordinate values of the second specific point on the lateral axis of the second bone in the YOZ plane are acquired.

In this embodiment, the first bone 22 is taken as an example. The doctor selects a first specific point P1 on the axis 222 of the first bone 22, and acquires coordinate values (x1, z1) of the first specific point P1 on the anteroposterior axis of the first bone in the XOZ plane and coordinate values (y2, z2) of the first specific point P1 on the lateral axis of the first bone in the YOZ plane.

In 210, a vector of the axis of the first bone in the spatial coordinate system is acquired based on the coordinate values of the first specific point of the first bone on the anteroposterior axis in the XOZ plane, the vector of the anteroposterior axis of the first bone in the XOZ plane, the coordinate values of the first specific point of the first bone on the lateral axis in the YOZ plane, and the vector of the lateral axis of the first bone in the YOZ plane; and a vector of the axis of the second bone in the spatial coordinate system is acquired based on the coordinate values of the second specific point of the second bone on the anteroposterior axis in the XOZ plane, the vector of the anteroposterior axis of the second bone in the XOZ plane, the coordinate values of the second specific point of the second bone on the lateral axis in the YOZ plane, and the vector of the lateral axis of the second bone in the YOZ plane.

As shown in FIG. 8, in this embodiment, the first bone 22 is taken as an example. The following formulas are acquired based on the vector (Vx, Vz) of the anteroposterior axis in the XOZ plane, the vector (Nx, Nz) of the lateral axis in the YOZ plane, the coordinate values (x1, z1) of the first specific point P1 on the anteroposterior axis in the XOZ plane, and the coordinate values (y2, z2) of the first specific point P1 on the lateral axis in the YOZ plane.

$$\frac{(x-x1)}{Vx} = \frac{(z-z1)}{Vz} \quad \text{Formula (1)}$$

$$\frac{(y-y2)}{Ny} = \frac{(z-z2)}{Nz} \quad \text{Formula (2)}$$

The vector $$\vec{V}_1 = \left(Vx, \frac{Ny \cdot X \cdot Vz}{Nz}, Vz\right)$$

of the axis 222 of the first bone 22 in the spatial coordinate system is acquired by combining the formula (1) with the formula (2), and the vector $\vec{V}_2$ of the axis 242 of the second bone 24 in the spatial coordinate system is acquired by the same processes and method.

In 211, an included angle between the first bone and the second bone in space is determined based on the vector of the axis of the first bone in the spatial coordinate system and the vector of the axis of the second bone in the spatial coordinate system.

In this embodiment, $$\cos\theta = \frac{\vec{V}_1 \cdot \vec{V}_2}{|\vec{V}_1| \cdot |\vec{V}_2|}$$

is acquired based on the vector $\vec{V}_1$ of the axis 222 of the first bone 22 in the spatial coordinate system and the vector $\vec{V}_2$ of the axis 242 of the second bone 24 in the spatial coordinate system, such that the included angle θ between the axis 222 of the first bone 22 and the axis 242 of the second bone 24 in space can be acquired. The included angle θ between the axis 222 of the first bone 22 and the axis 242 of the second bone 24 in space is the included angle θ between the first bone 22 and the second bone 24 in space. Therefore, a fracture reduction direction is directly acquired based on the included angle between two bones, and a moving process may be directly performed based on the direction. In the case that the first bone 22 and the second bone 24 are at a same line, the distance d between the first bone 22 and the second bone 24 may be reduced by movement, so as to achieve contact of the first bone 22 and the second bone 24. Therefore, the fracture reduction processes are simplified, the precision of bone alignment is improved, the operation effect is improved, and the occurrence of a secondary fracture is prevented.

The above method may also be configured for detection after completion of bone setting, that is, the method may be configured to detect whether there is still an included angle between the first bone 22 and the second bone 24 after completion of bone setting.

FIG. 9 is a structural schematic diagram of a computer-aided apparatus for fracture reduction according to an embodiment of the present disclosure. As shown in FIG. 9, the apparatus includes an acquiring module 301, a first determining module 302 and a second determining module 303.

The acquiring module 301 is configured to acquire an anteroposterior image and a lateral image of a fracture site, wherein the anteroposterior image includes an anteroposterior image of a first bone and an anteroposterior image of a second bone, and the lateral image includes a lateral image of the first bone and a lateral image of the second bone, the first bone and the second bone being two bones at the fracture site.

The first determining module 302 is configured to determine a vector of an axis of the first bone in a spatial coordinate system based on the anteroposterior image of the first bone and the lateral image of the first bone, and determine a vector of an axis of the second bone in the spatial coordinate system based on the anteroposterior image of the second bone and the lateral image of the second bone.

The second determining module 303 is configured to determine an included angle between the first bone and the second bone in space based on the vector of the axis of the first bone in the spatial coordinate system and the vector of the axis of the second bone in the spatial coordinate system, wherein the included angle is configured to indicate a fracture reduction direction.

Optionally, the first determining module 302 includes:

a first determining unit 321, configured to acquire an actual equation of an anteroposterior axis of the first bone based on the anteroposterior image of the first bone, and acquire an actual equation of a lateral axis of the first bone based on the lateral image of the first bone; and determine the vector of the axis of the first bone in the spatial coordinate system based on the actual equation of the anteroposterior axis of the first bone and the actual equation of the lateral axis of the first bone; and a second determining unit 322, configured to acquire an actual equation of an anteroposterior axis of the second bone based on the anteroposterior image of the second bone, and acquire an actual equation of a lateral axis of the second bone based on the lateral image of the second bone; and determine the vector of the axis of the second bone in the spatial coordinate system based on the actual equation of the anteroposterior axis of the second bone and the actual equation of the lateral axis of the second bone.

Optionally, the first determining unit 321 is configured to acquire coordinate values of a plurality of pixel points in an anteroposterior fracture boundary region of the first bone based on the anteroposterior image of the first bone, and acquire coordinate values of a plurality of pixel points in a lateral fracture boundary region of the first bone based on the lateral image of the first bone; and calculate the actual equation of the anteroposterior axis of the first bone based on the coordinate values of the plurality of pixel points in the anteroposterior fracture boundary region of the first bone, and calculate the actual equation of the lateral axis of the first bone based on the coordinate values of the plurality of pixel points in the lateral fracture boundary region of the first bone; and the second determining unit 322 is configured to acquire coordinate values of a plurality of pixel points in an anteroposterior fracture boundary region of the second bone based on the anteroposterior image of the second bone, and acquire coordinate values of a plurality of pixel points in the lateral fracture boundary region of the second bone based on the lateral image of the second bone; and calculate the actual equation of the anteroposterior axis of the second bone based on the coordinate values of the plurality of pixel points in the anteroposterior fracture boundary region of the second bone, and calculate the actual equation of the lateral axis of the second bone based on the coordinate values of the plurality of pixel points in the lateral fracture boundary region of the second bone.

Optionally, the first determining unit 321 is configured to acquire the anteroposterior fracture boundary region of the first bone based on the anteroposterior image of the first bone, and acquire the lateral fracture boundary region of the first bone based on the lateral image of the first bone; and acquire the coordinate values of the plurality of pixel points in the anteroposterior fracture boundary region of the first bone, and acquire the coordinate values of the plurality of pixel points in the lateral fracture boundary region of the first bone; and the second determining unit 322 is configured to acquire the anteroposterior fracture boundary region of the second bone based on the anteroposterior image of the second bone, and acquire the lateral fracture boundary region of the second bone based on the lateral image of the second bone; and acquire the coordinate values of the plurality of pixel points of the anteroposterior fracture boundary region of the second bone, and acquire the coordinate values of the plurality of pixel points in the lateral fracture boundary region of the second bone.

Optionally, the first determining unit 321 is configured to acquire an anteroposterior boundary region of the first bone based on the anteroposterior image of the first bone, and acquire a lateral boundary region of the first bone based on the lateral image of the first bone; and select the anteroposterior fracture boundary region of the first bone from the anteroposterior boundary region of the first bone, and select the lateral fracture boundary region of the first bone from the lateral boundary region of the first bone; and the second determining unit 322 is configured to acquire an anteroposterior boundary region of the second bone based on the anteroposterior image of the second bone, and acquire a lateral boundary region of the second bone based on the lateral image of the second bone; and select the anteroposterior fracture boundary region of the second bone from the anteroposterior boundary region of the second bone, and select the lateral fracture boundary region of the second bone from the lateral boundary region of the second bone.

Optionally, the first determining unit 321 is configured to acquire an anteroposterior axis equation of the first bone, and acquire a lateral axis equation of the first bone; and calculate the actual equation of the anteroposterior axis of the first bone through a least squares algorithm based on the coordinate values of the plurality of pixel points in the anteroposterior fracture boundary region of the first bone and the acquired anteroposterior axis equation of the first bone, and calculate the actual equation of the lateral axis of the first bone through the least squares algorithm based on the coordinate values of the plurality of pixel points in the lateral fracture boundary region of the first bone and the acquired lateral axis equation of the first bone; and the second determining unit 322 is configured to acquire an anteroposterior axis equation of the second bone, and acquire a lateral axis equation of the second bone; and calculate the actual equation of the anteroposterior axis of the second bone through the least squares algorithm based on the coordinate values of the plurality of pixel points in the anteroposterior fracture boundary region of the second bone and the acquired anteroposterior axis equation of the second bone, and calculate the actual equation of the lateral axis of the second bone through the least squares algorithm based on the coordinate values of the plurality of pixel points in the lateral fracture boundary region of the second bone and the acquired lateral axis equation of the second bone.

Optionally, a plane in which the anteroposterior image of the first bone and the anteroposterior image of the second bone are disposed is an XOZ plane, and a plane in which the lateral image of the first bone and the lateral image of the second bone are disposed is a YOZ plane;

the first determining unit 321 is configured to acquire a vector of the anteroposterior axis of the first bone in the XOZ plane based on the actual equation of the anteroposterior axis of the first bone, and acquire a vector of the lateral axis of the first bone in the YOZ plane based on the actual equation of the lateral axis of the first bone; select a first specific point on the axis of the first bone, and acquire coordinate values of the first specific point on the anteroposterior axis of the first bone in the XOZ plane and coordinate values of the first specific point on the lateral axis of the first bone in the YOZ plane; and acquire the vector of the axis of the first bone in the spatial coordinate system based on the coordinate values of the first specific point of the first bone on the anteroposterior axis in the XOZ plane, the vector of the anteroposterior axis of the first bone in the XOZ plane, the coordinate values of the first specific point of the first bone on the lateral axis in the YOZ plane and the vector of the lateral axis of the first bone in the YOZ plane; and the second determining unit 322 is configured to acquire a vector of the anteroposterior axis of the second bone in the XOZ plane based on the actual equation of the anteroposterior axis of the second bone, and acquire a vector of the lateral axis of the second bone in the YOZ plane based on the actual equation of the lateral axis of the second bone; select a second specific point on the axis of the second bone, and acquire coordinate values of the second specific point on the anteroposterior axis of the second bone in the XOZ plane and coordinate values of the second specific point on the lateral axis of the second bone in the YOZ plane; and acquire the vector of the axis of the second bone in the spatial coordinate system based on the coordinate values of the second specific point of the second bone on the anteroposterior axis in the XOZ plane, the vector of the anteroposterior axis of the second bone in the XOZ plane, the coordinate values of the second specific point of the second bone on the lateral axis in the YOZ plane and the vector of the lateral axis of the second bone in the YOZ plane.

FIG. 10 is a structural block diagram of an electronic device according to an embodiment of the present disclosure. Generally, the electronic device includes a processor 401 and a memory 402.

The processor 401 may include one or more processing cores, such as a 4-core processor and an 8-core processor. The processor 401 may adopt at least one hardware form of digital signal processing (DSP), field-programmable gate array (FPGA), and programmable logic array (PLA). The processor 401 may further include a main processor and a co-processor. The main processor, which is also referred to as a central processing unit (CPU), is a processor that processes data in an awake state; and the co-processor is a low-power processor configured to process data in a standby state.

The memory 402 may include one or more computer readable storage media, wherein the computer readable storage medium may be non-transitory. The memory 402 may further include a high-speed random access memory and a non-volatile memory, such as one or more magnetic disk storage devices and flash memory storage devices. In some embodiments, the non-transitory computer readable storage medium in the memory 402 is configured to store at least one instruction, wherein the at least one instruction, when run by the processor 401, causes the processor to perform the computer-aided method for fracture reduction according to embodiments of the present disclosure.

As shown in FIG. 3, an embodiment of the present disclosure provides a G-arm X-ray device 1. The device includes a front-view X-ray portion 12, a side-view X-ray portion 14, and the above controller. The front-view X-ray portion 12 is configured to capture an anteroposterior image of a fracture site 2, and the side-view X-ray portion 14 is configured to capture a lateral image of the fracture site 2, wherein the anteroposterior image and the lateral image are transmitted to the controller.

The front-view X-ray portion 12 includes a front-view X-ray source and a front-view receiver; wherein the front-view X-ray source and the front-view receiver are disposed at upper and lower sides of the fracture site 2 respectively. The front-view X-ray source is configured to emit an X-ray to a bone, and the front-view receiver receives the anteroposterior image of the fracture site 2 irradiated by the X-ray. The side-view X-ray portion 14 includes a side-view X-ray source and a side-view receiver, wherein the side-view X-ray source and the side-view receiver are disposed at left and right sides of the fracture site 2 respectively; wherein the side-view X-ray source is configured to emit an X-ray to the fracture site 2, and the side-view receiver receives the lateral image of the bone irradiated by the X-ray.

In this embodiment, the G-arm X-ray device 1 further includes a fixator, a movable table 18, and a display device; wherein the fixator 16 is configured to fix the fracture site 2, the movable table is disposed below the G-arm X-ray device 1 to move the G-arm X-ray device 1, and the display device is configured to display the first bone 22 and the second bone 24 on a screen by three-dimensional virtual simulation and display an indication animation of simulating reduction in a virtual simulation environment. In this way, the doctor may determine the reduction direction more visibly and move the bones of the patient to a substantially aligned position based on the three-dimensional virtual simulation and an included angle between the first bone 22 and the second bone 24 in a spatial coordinate system, and then capture an image again for next fine adjustment. This method reduces the number of capturing by X-ray and reduces risks of radiation to the doctor and the patient.

The controller may be a microcontroller unit (MCU), or the like. The principle of the function of the controller and the computer-aided method for fracture reduction are same as those in the above embodiments, which are not repeated herein.

The persons skilled in the art should understand that the embodiments of the present disclosure may be provided as a method, a system or a computer program product through the above descriptions of embodiments. Thus, entire hardware embodiments, entire software embodiments or embodiments combining software and hardware may be adopted in the present disclosure. Further, the present disclosure may be implemented in the form of a computer program product that is operated on one or more computer available storage media (including but not limited to a magnetic disk memory, a compact disc read-only memory (CD-ROM), an optical memory, and the like) including computer available program codes.

The present disclosure is described by referring to flowcharts and/or block diagrams of a method, a device (a system), and a computer program product in embodiments of the present disclosure. It is to be understood that each flow and/or block in the flowchart and/or the block diagram, or a combination of flows and/or blocks in the flowcharts and/or the block diagrams may be implemented through computer program instructions. These computer program instructions may be provided to a general-purpose computer, a dedicated computer, an embedded processor, or a processor of other programmable data processing device to generate a machine, such that an apparatus, configured for implementing functions designated in one or more flows of the flowcharts and/or one or more blocks of the block diagrams, can be defined by the instructions executable by the computer or the processor of another programmable data processing device.

These computer program instructions may also be stored in a computer readable memory that may guide a computer or other programmable data processing device to work in a particular fashion, such that a product including an instruction apparatus can be defined by the instructions stored in the computer readable memory, wherein the instruction apparatus can achieve functions designated in one or more flows of the flowcharts and/or one or more blocks of the block diagrams.

These computer program instructions may also be loaded on a computer or other programmable data processing device, such that a series of operation processes are performed on the computer or other programmable device to achieve specific functions, that is, the instructions executable on the computer or other programmable data processing device provide processes for implementing functions designated in one or more flows of the flowcharts and/or one or more blocks of the block diagrams.

In a typical configuration, a computing device includes one or more processors (CPU), input/output interfaces, network interfaces, and memories.

The memory may include a non-permanent memory, a random-access memory (RAM), and/or a non-volatile memory among computer readable mediums, such as a read-only memory (ROM) or a flash memory (flash RAM). The memory is an example of the computer readable medium.

The computer readable medium includes permanent, non-permanent, mobile and non-mobile media, which may realize information storage by any method or technology. The information may be computer readable instructions, data structures, program modules, and other data. Examples of the computer storage medium include but are not limited to: a phase change random access memory (PRAM), a static random access memory (SRAM), a dynamic random access memory (DRAM), and other types of random access memories (RAMs), read-only memories (ROMs), electrically-erasable programmable read-only memories (EEPROM), flash memories, or other memory technologies, compact-disc read only memories (CD-ROMs), digital versatile discs (DVD) or other optical storage devices, cassette-type magnetic tapes, magnetic disk storage devices, or other magnetic storage devices, or any other non-transitory media for storing information accessible by the computing device. According to a definition of the specification, the computer readable medium does not include transitory computer readable media, such as modulated data signals and carriers.

The computer-aided method for fracture reduction according to embodiments of the present disclosure includes:

acquiring an anteroposterior image and a lateral image of a fracture site, wherein in a severe fracture, the fracture refers to two bones that have certain angular deviation; the fractured site includes a first bone and a second bone, the anteroposterior image includes an anteroposterior image of the first bone and an anteroposterior image of the second bone, and the lateral image includes a lateral image of the first bone and a lateral image of the second bone;

acquiring vectors of an axis of the first bone and an axis of the second bone in a spatial coordinate system by determining the vector of the axis of the first bone in the spatial coordinate system based on the anteroposterior image of the first bone and the lateral image of the first bone and determining the vector of the axis of the second bone in the spatial coordinate system based on the anteroposterior image of the second bone and the lateral image of the second bone; and determining an included angle between the first bone and the second bone in space based on the vectors of the first bone and the second bone in the spatial coordinate system, wherein the included angle between the first bone and the second bone in space is a rotation angle of the second bone relative to the first bone.

Thus, a direction of fracture reduction may be directly acquired based on the included angle between two bones, and a moving process may be directly performed based on the direction. Therefore, the fracture reduction processes are simplified, a precision of bone alignment is improved, an accuracy of a subsequent operation and an operation effect are improved, and the occurrence of a secondary fracture is prevented.

Described above are merely specific embodiments of the present disclosure, and are not intended to limit the scope of protection of the present disclosure. Any changes or substitutions that can be easily derived by the persons skilled in the art in the technical scope of the present disclosure should fall in the scope of protection of the present disclosure. Therefore, the scope of protection of the present disclosure is indicated as in the appended claims.

What is claimed is:

1. A computer-aided method for fracture reduction, comprising:

acquiring an anteroposterior image and a lateral image of a fracture site, wherein the anteroposterior image comprises an anteroposterior image of a first bone and an anteroposterior image of a second bone, and the lateral image comprises a lateral image of the first bone and a lateral image of the second bone, the first bone and the second bone being two bones at the fracture site;

determining a vector of an axis of the first bone in a spatial coordinate system based on the anteroposterior image and the lateral image of the first bone, and determining a vector of an axis of the second bone in the spatial coordinate system based on the anteroposterior image of the second bone and the lateral image of the second bone; and determining an included angle between the first bone and the second bone in the spatial coordinate system based on the vector of the axis of the first bone in the spatial coordinate system and the vector of the axis of the second bone in the spatial coordinate system, wherein the included angle is configured to indicate a direction of fracture reduction;

wherein determining the vector of the axis of the first bone in the spatial coordinate system based on the anteroposterior image and the lateral image of the first bone comprises:

acquiring an actual equation of an anteroposterior axis of the first bone based on the anteroposterior image of the first bone, and acquiring an actual equation of a lateral axis of the first bone based on the lateral image of the first bone; and determining the vector of the axis of the first bone in the spatial coordinate system based on the actual equation of the anteroposterior axis of the first bone and the actual equation of the lateral axis of the first bone; and determining the vector of the axis of the second bone in the spatial coordinate system based on the anteroposterior image of the second bone and the lateral image of the second bone comprises:

acquiring an actual equation of an anteroposterior axis of the second bone based on the anteroposterior image of the second bone, and acquiring an actual equation of a lateral axis of the second bone based on the lateral image of the second bone; and determining the vector of the axis of the second bone in the spatial coordinate system based on the actual equation of the anteroposterior axis of the second bone and the actual equation of the lateral axis of the second bone.

2. The method according to claim 1, wherein acquiring the actual equation of the anteroposterior axis of the first bone based on the anteroposterior image of the first bone, and acquiring the actual equation of the lateral axis of the first bone based on the lateral image of the first bone comprise:

acquiring coordinate values of a plurality of pixel points in an anteroposterior fracture boundary region of the first bone based on the anteroposterior image of the first bone, and acquiring coordinate values of a plurality of pixel points in a lateral fracture boundary region of the first bone based on the lateral image of the first bone; and calculating the actual equation of the anteroposterior axis of the first bone based on the coordinate values of the plurality of pixel points in the anteroposterior fracture boundary region of the first bone, and calculating the actual equation of the lateral axis of the first bone based on the coordinate values of the plurality of pixel points in the lateral fracture boundary region of the first bone; and acquiring the actual equation of the anteroposterior axis of the second bone based on the anteroposterior image of the second bone, and acquiring the actual equation of the lateral axis of the second bone based on the lateral image of the second bone comprise:

acquiring coordinate values of a plurality of pixel points in an anteroposterior fracture boundary region of the second bone based on the anteroposterior image of the second bone, and acquiring coordinate values of a plurality of pixel points in a lateral fracture boundary region of the second bone based on the lateral image of the second bone; and calculating the actual equation of the anteroposterior axis of the second bone based on the coordinate values of the plurality of pixel points in the anteroposterior fracture boundary region of the second bone, and calculating the actual equation of the lateral axis of the second bone based on the coordinate values of the plurality of pixel points in the lateral fracture boundary region of the second bone.

3. The method according to claim 2, wherein acquiring the coordinate values of the plurality of pixel points in the anteroposterior fracture boundary region of the first bone based on the anteroposterior image of the first bone, and acquiring the coordinate values of the plurality of pixel points in the lateral fracture boundary region of the first bone based on the lateral image of the first bone comprise:

acquiring the anteroposterior fracture boundary region of the first bone based on the anteroposterior image of the first bone, and acquiring the lateral fracture boundary region of the first bone based on the lateral image of the first bone; and acquiring the coordinate values of the plurality of pixel points in the anteroposterior fracture boundary region of the first bone, and acquiring the coordinate values of the plurality of pixel points in the lateral fracture boundary region of the first bone; and acquiring the coordinate values of the plurality of pixel points in the anteroposterior fracture boundary region of the second bone based on the anteroposterior image of the second bone, and acquiring the coordinate values of the plurality of pixel points in the lateral fracture boundary region of the second bone based on the lateral image of the second bone comprise:

acquiring the anteroposterior fracture boundary region of the second bone based on the anteroposterior image of the second bone, and acquiring the lateral fracture boundary region of the second bone based on the lateral image of the second bone; and acquiring the coordinate values of the plurality of pixel points in the anteroposterior fracture boundary region of the second bone, and acquiring the coordinate values of the plurality of pixel points in the lateral fracture boundary region of the second bone.

4. The method according to claim 3, wherein acquiring the anteroposterior fracture boundary region of the first bone based on the anteroposterior image of the first bone, and acquiring the lateral fracture boundary region of the first bone based on the lateral image of the first bone comprise:

acquiring an anteroposterior boundary region of the first bone based on the anteroposterior image of the first bone, and acquiring a lateral boundary region of the first bone based on the lateral image of the first bone; and selecting the anteroposterior fracture boundary region of the first bone from the anteroposterior boundary region of the first bone, and selecting the lateral fracture boundary region of the first bone from the lateral boundary region of the first bone; and acquiring the anteroposterior fracture boundary region of the second bone based on the anteroposterior image of the second bone, and acquiring the lateral fracture boundary region of the second bone based on the lateral image of the second bone comprise:

acquiring an anteroposterior boundary region of the second bone based on the anteroposterior image of the second bone, and acquiring a lateral boundary region of the second bone based on the lateral image of the second bone; and selecting the anteroposterior fracture boundary region of the second bone from the anteroposterior boundary region of the second bone, and selecting the lateral fracture boundary region of the second bone from the lateral boundary region of the second bone.

5. The method according to claim 2, wherein calculating the actual equation of the anteroposterior axis of the first bone based on the coordinate values of the plurality of pixel points in the anteroposterior fracture boundary region of the first bone, and calculating the actual equation of the lateral axis of the first bone based on the coordinate values of a plurality of pixel points in the lateral fracture boundary region of the first bone comprise:
acquiring an anteroposterior axis equation of the first bone, and acquiring a lateral axis equation of the first bone; and
calculating the actual equation of the anteroposterior axis of the first bone through a least squares algorithm based on the coordinate values of the plurality of pixel points in the anteroposterior fracture boundary region of the first bone and the acquired anteroposterior axis equation of the first bone, and calculating the actual equation of the lateral axis of the first bone through the least squares algorithm based on the coordinate values of the plurality of pixel points in the lateral fracture boundary region of the first bone and the acquired lateral axis equation of the first bone; and
calculating the actual equation of the anteroposterior axis of the second bone based on the coordinate values of the plurality of pixel points in the anteroposterior fracture boundary region of the second bone, and calculating the actual equation of the lateral axis of the second bone based on the coordinate values of the plurality of pixel points in the lateral fracture boundary region of the second bone comprise:
acquiring an anteroposterior axis equation of the second bone, and acquiring a lateral axis equation of the second bone; and
calculating the actual equation of the anteroposterior axis of the second bone through the least squares algorithm based on the coordinate values of the plurality of pixel points in the anteroposterior fracture boundary region of the second bone and the acquired anteroposterior axis equation of the second bone, and calculating the actual equation of the lateral axis of the second bone through the least squares algorithm based on the coordinate values of the plurality of pixel points in the lateral fracture boundary region of the second bone and the acquired lateral axis equation of the second bone.

6. The method according to claim 3, wherein a plane in which the anteroposterior image of the first bone and the anteroposterior image of the second bone are disposed is an XOZ plane, and a plane in which the lateral image of the first bone and the lateral image of the second bone are disposed is a YOZ plane;
determining the vector of the axis of the first bone in the spatial coordinate system based on the actual equation of the anteroposterior axis of the first bone and the actual equation of the lateral axis of the first bone comprises:
acquiring a vector of the anteroposterior axis of the first bone in the XOZ plane based on the actual equation of the anteroposterior axis of the first bone, and acquiring a vector of the lateral axis of the first bone in the YOZ plane based on the actual equation of the lateral axis of the first bone;
selecting a first specific point on the axis of the first bone, and acquiring coordinate values of the first specific point on the anteroposterior axis of the first bone in the XOZ plane and coordinate values of the first specific point on the lateral axis of the first bone in the YOZ plane; and
acquiring the vector of the axis of the first bone in the spatial coordinate system based on the coordinate values of the first specific point of the first bone on the anteroposterior axis in the XOZ plane, the vector of the anteroposterior axis of the first bone in the XOZ plane, the coordinate values of the first specific point of the first bone on the lateral axis in the YOZ plane and the vector of the lateral axis of the first bone in the YOZ plane; and
determining the vector of the axis of the second bone in the spatial coordinate system based on the actual equation of the anteroposterior axis of the second bone and the actual equation of the lateral axis of the second bone comprises:
acquiring a vector of the anteroposterior axis of the second bone in the XOZ plane based on the actual equation of the anteroposterior axis of the second bone, and acquiring a vector of the lateral axis of the second bone in the YOZ plane based on the actual equation of the lateral axis of the second bone;
selecting a second specific point on the axis of the second bone, and acquiring coordinate values of the second specific point on the anteroposterior axis of the second bone in the XOZ plane and coordinate values of the second specific point on the lateral axis of the second bone in the YOZ plane; and
acquiring the vector of the axis of the second bone in the spatial coordinate system based on the coordinate values of the second specific point of the second bone on the anteroposterior axis in the XOZ plane, the vector of the anteroposterior axis of the second bone in the XOZ plane, the coordinate values of the second specific point of the second bone on the lateral axis in the YOZ plane and the vector of the lateral axis of the second bone in the YOZ plane.

7. An electronic device, comprising a memory storing at least one program code therein and a processor; wherein the program code, when loaded and executed by the processor, causes the processor to perform a computer-aided method for fracture reduction, wherein the method comprises:
acquiring an anteroposterior image and a lateral image of a fracture site, wherein the anteroposterior image comprises an anteroposterior image of a first bone and an anteroposterior image of a second bone, and the lateral image comprises a lateral image of the first bone and a lateral image of the second bone, the first bone and the second bone being two bones at the fracture site;
determining a vector of an axis of the first bone in a spatial coordinate system based on the anteroposterior image and the lateral image of the first bone, and determining a vector of an axis of the second bone in the spatial coordinate system based on the anteroposterior image of the second bone and the lateral image of the second bone; and
determining an included angle between the first bone and the second bone in the spatial coordinate system based on the vector of the axis of the first bone in the spatial coordinate system and the vector of the axis of the second bone in the spatial coordinate system, wherein the included angle is configured to indicate a direction of fracture reduction;
wherein determining the vector of the axis of the first bone in the spatial coordinate system based on the anteroposterior image and the lateral image of the first bone comprises:
acquiring an actual equation of an anteroposterior axis of the first bone based on the anteroposterior image of the first bone, and acquiring an actual equation of a lateral axis of the first bone based on the lateral image of the first bone; and determining the vector of the axis of the first bone in the spatial coordinate system based on the actual equation of the anteroposterior axis of the first bone and the actual equation of the lateral axis of the first bone; and determining the vector of the axis of the second bone in the spatial coordinate system based on the anteroposterior image of the second bone and the lateral image of the second bone comprises:

acquiring an actual equation of an anteroposterior axis of the second bone based on the anteroposterior image of the second bone, and acquiring an actual equation of a lateral axis of the second bone based on the lateral image of the second bone; and determining the vector of the axis of the second bone in the spatial coordinate system based on the actual equation of the anteroposterior axis of the second bone and the actual equation of the lateral axis of the second bone.

8. The device according to claim 7, wherein acquiring the actual equation of the anteroposterior axis of the first bone based on the anteroposterior image of the first bone, and acquiring the actual equation of the lateral axis of the first bone based on the lateral image of the first bone comprise:

acquiring coordinate values of a plurality of pixel points in an anteroposterior fracture boundary region of the first bone based on the anteroposterior image of the first bone, and acquiring coordinate values of a plurality of pixel points in a lateral fracture boundary region of the first bone based on the lateral image of the first bone; and calculating the actual equation of the anteroposterior axis of the first bone based on the coordinate values of the plurality of pixel points in the anteroposterior fracture boundary region of the first bone, and calculating the actual equation of the lateral axis of the first bone based on the coordinate values of the plurality of pixel points in the lateral fracture boundary region of the first bone; and acquiring the actual equation of the anteroposterior axis of the second bone based on the anteroposterior image of the second bone, and acquiring the actual equation of the lateral axis of the second bone based on the lateral image of the second bone comprise:

acquiring coordinate values of a plurality of pixel points in an anteroposterior fracture boundary region of the second bone based on the anteroposterior image of the second bone, and acquiring coordinate values of a plurality of pixel points in a lateral fracture boundary region of the second bone based on the lateral image of the second bone; and calculating the actual equation of the anteroposterior axis of the second bone based on the coordinate values of the plurality of pixel points in the anteroposterior fracture boundary region of the second bone, and calculating the actual equation of the lateral axis of the second bone based on the coordinate values of the plurality of pixel points in the lateral fracture boundary region of the second bone.

9. The device according to claim 8, wherein acquiring the coordinate values of the plurality of pixel points in the anteroposterior fracture boundary region of the first bone based on the anteroposterior image of the first bone, and acquiring the coordinate values of the plurality of pixel points in the lateral fracture boundary region of the first bone based on the lateral image of the first bone comprise:

acquiring the anteroposterior fracture boundary region of the first bone based on the anteroposterior image of the first bone, and acquiring the lateral fracture boundary region of the first bone based on the lateral image of the first bone; and acquiring the coordinate values of the plurality of pixel points in the anteroposterior fracture boundary region of the first bone, and acquiring the coordinate values of the plurality of pixel points in the lateral fracture boundary region of the first bone; and acquiring the coordinate values of the plurality of pixel points in the anteroposterior fracture boundary region of the second bone based on the anteroposterior image of the second bone, and acquiring the coordinate values of the plurality of pixel points in the lateral fracture boundary region of the second bone based on the lateral image of the second bone comprise:

acquiring the anteroposterior fracture boundary region of the second bone based on the anteroposterior image of the second bone, and acquiring the lateral fracture boundary region of the second bone based on the lateral image of the second bone; and acquiring the coordinate values of the plurality of pixel points in the anteroposterior fracture boundary region of the second bone, and acquiring the coordinate values of the plurality of pixel points in the lateral fracture boundary region of the second bone.

10. The device according to claim 9, wherein acquiring the anteroposterior fracture boundary region of the first bone based on the anteroposterior image of the first bone, and acquiring the lateral fracture boundary region of the first bone based on the lateral image of the first bone comprise:

acquiring an anteroposterior boundary region of the first bone based on the anteroposterior image of the first bone, and acquiring a lateral boundary region of the first bone based on the lateral image of the first bone; and selecting the anteroposterior fracture boundary region of the first bone from the anteroposterior boundary region of the first bone, and selecting the lateral fracture boundary region of the first bone from the lateral boundary region of the first bone; and acquiring the anteroposterior fracture boundary region of the second bone based on the anteroposterior image of the second bone, and acquiring the lateral fracture boundary region of the second bone based on the lateral image of the second bone comprise:

acquiring an anteroposterior boundary region of the second bone based on the anteroposterior image of the second bone, and acquiring a lateral boundary region of the second bone based on the lateral image of the second bone; and selecting the anteroposterior fracture boundary region of the second bone from the anteroposterior boundary region of the second bone, and selecting the lateral fracture boundary region of the second bone from the lateral boundary region of the second bone.

11. The device according to claim 8, wherein calculating the actual equation of the anteroposterior axis of the first bone based on the coordinate values of the plurality of pixel points in the anteroposterior fracture boundary region of the first bone, and calculating the actual equation of the lateral axis of the first bone based on the coordinate values of a plurality of pixel points in the lateral fracture boundary region of the first bone comprise:
acquiring an anteroposterior axis equation of the first bone, and acquiring a lateral axis equation of the first bone; and
calculating the actual equation of the anteroposterior axis of the first bone through a least squares algorithm based on the coordinate values of the plurality of pixel points in the anteroposterior fracture boundary region of the first bone and the acquired anteroposterior axis equation of the first bone, and calculating the actual equation of the lateral axis of the first bone through the least squares algorithm based on the coordinate values of the plurality of pixel points in the lateral fracture boundary region of the first bone and the acquired lateral axis equation of the first bone; and
calculating the actual equation of the anteroposterior axis of the second bone based on the coordinate values of the plurality of pixel points in the anteroposterior fracture boundary region of the second bone, and calculating the actual equation of the lateral axis of the second bone based on the coordinate values of the plurality of pixel points in the lateral fracture boundary region of the second bone comprise:
acquiring an anteroposterior axis equation of the second bone, and acquiring a lateral axis equation of the second bone; and
calculating the actual equation of the anteroposterior axis of the second bone through the least squares algorithm based on the coordinate values of the plurality of pixel points in the anteroposterior fracture boundary region of the second bone and the acquired anteroposterior axis equation of the second bone, and calculating the actual equation of the lateral axis of the second bone through the least squares algorithm based on the coordinate values of the plurality of pixel points in the lateral fracture boundary region of the second bone and the acquired lateral axis equation of the second bone.

12. The device according to claim 9, wherein a plane in which the anteroposterior image of the first bone and the anteroposterior image of the second bone are disposed is an XOZ plane, and a plane in which the lateral image of the first bone and the lateral image of the second bone are disposed is a YOZ plane;
determining the vector of the axis of the first bone in the spatial coordinate system based on the actual equation of the anteroposterior axis of the first bone and the actual equation of the lateral axis of the first bone comprises:
acquiring a vector of the anteroposterior axis of the first bone in the XOZ plane based on the actual equation of the anteroposterior axis of the first bone, and acquiring a vector of the lateral axis of the first bone in the YOZ plane based on the actual equation of the lateral axis of the first bone;
selecting a first specific point on the axis of the first bone, and acquiring coordinate values of the first specific point on the anteroposterior axis of the first bone in the XOZ plane and coordinate values of the first specific point on the lateral axis of the first bone in the YOZ plane; and
acquiring the vector of the axis of the first bone in the spatial coordinate system based on the coordinate values of the first specific point of the first bone on the anteroposterior axis in the XOZ plane, the vector of the anteroposterior axis of the first bone in the XOZ plane, the coordinate values of the first specific point of the first bone on the lateral axis in the YOZ plane and the vector of the lateral axis of the first bone in the YOZ plane; and
determining the vector of the axis of the second bone in the spatial coordinate system based on the actual equation of the anteroposterior axis of the second bone and the actual equation of the lateral axis of the second bone comprises:
acquiring a vector of the anteroposterior axis of the second bone in the XOZ plane based on the actual equation of the anteroposterior axis of the second bone, and acquiring a vector of the lateral axis of the second bone in the YOZ plane based on the actual equation of the lateral axis of the second bone;
selecting a second specific point on the axis of the second bone, and acquiring coordinate values of the second specific point on the anteroposterior axis of the second bone in the XOZ plane and coordinate values of the second specific point on the lateral axis of the second bone in the YOZ plane; and
acquiring the vector of the axis of the second bone in the spatial coordinate system based on the coordinate values of the second specific point of the second bone on the anteroposterior axis in the XOZ plane, the vector of the anteroposterior axis of the second bone in the XOZ plane, the coordinate values of the second specific point of the second bone on the lateral axis in the YOZ plane and the vector of the lateral axis of the second bone in the YOZ plane.

13. A G-arm X-ray device, comprising a front-view X-ray portion, a side-view X-ray portion, and a controller; wherein
the front-view X-ray portion is configured to capture an anteroposterior image of a fracture site, and the side-view X-ray portion is configured to capture a lateral image of the fracture site, wherein the anteroposterior image and the lateral image are transmitted to the controller; and
the controller is configured to perform a computer-aided method for fracture reduction;
wherein the method comprises:
acquiring an anteroposterior image and a lateral image of a fracture site, wherein the anteroposterior image comprises an anteroposterior image of a first bone and an anteroposterior image of a second bone, and the lateral image comprises a lateral image of the first bone and a lateral image of the second bone, the first bone and the second bone being two bones at the fracture site;
determining a vector of an axis of the first bone in a spatial coordinate system based on the anteroposterior image and the lateral image of the first bone, and determining a vector of an axis of the second bone in the spatial coordinate system based on the anteroposterior image of the second bone and the lateral image of the second bone; and
determining an included angle between the first bone and the second bone in the spatial coordinate system based on the vector of the axis of the first bone in the spatial coordinate system and the vector of the axis of the second bone in the spatial coordinate system, wherein the included angle is configured to indicate a direction of fracture reduction;

wherein determining the vector of the axis of the first bone in the spatial coordinate system based on the anteroposterior image and the lateral image of the first bone comprises:
- acquiring an actual equation of an anteroposterior axis of the first bone based on the anteroposterior image of the first bone, and acquiring an actual equation of a lateral axis of the first bone based on the lateral image of the first bone; and
- determining the vector of the axis of the first bone in the spatial coordinate system based on the actual equation of the anteroposterior axis of the first bone and the actual equation of the lateral axis of the first bone; and determining the vector of the axis of the second bone in the spatial coordinate system based on the anteroposterior image of the second bone and the lateral image of the second bone comprises:
- acquiring an actual equation of an anteroposterior axis of the second bone based on the anteroposterior image of the second bone, and acquiring an actual equation of a lateral axis of the second bone based on the lateral image of the second bone; and
- determining the vector of the axis of the second bone in the spatial coordinate system based on the actual equation of the anteroposterior axis of the second bone and the actual equation of the lateral axis of the second bone.

14. The device according to claim 13, wherein
acquiring the actual equation of the anteroposterior axis of the first bone based on the anteroposterior image of the first bone, and acquiring the actual equation of the lateral axis of the first bone based on the lateral image of the first bone comprise:
- acquiring coordinate values of a plurality of pixel points in an anteroposterior fracture boundary region of the first bone based on the anteroposterior image of the first bone, and acquiring coordinate values of a plurality of pixel points in a lateral fracture boundary region of the first bone based on the lateral image of the first bone; and
- calculating the actual equation of the anteroposterior axis of the first bone based on the coordinate values of the plurality of pixel points in the anteroposterior fracture boundary region of the first bone, and calculating the actual equation of the lateral axis of the first bone based on the coordinate values of the plurality of pixel points in the lateral fracture boundary region of the first bone; and acquiring the actual equation of the anteroposterior axis of the second bone based on the anteroposterior image of the second bone, and acquiring the actual equation of the lateral axis of the second bone based on the lateral image of the second bone comprise:
- acquiring coordinate values of a plurality of pixel points in an anteroposterior fracture boundary region of the second bone based on the anteroposterior image of the second bone, and acquiring coordinate values of a plurality of pixel points in a lateral fracture boundary region of the second bone based on the lateral image of the second bone; and
- calculating the actual equation of the anteroposterior axis of the second bone based on the coordinate values of the plurality of pixel points in the anteroposterior fracture boundary region of the second bone, and calculating the actual equation of the lateral axis of the second bone based on the coordinate values of the plurality of pixel points in the lateral fracture boundary region of the second bone.

15. The device according to claim 14, wherein
acquiring the coordinate values of the plurality of pixel points in the anteroposterior fracture boundary region of the first bone based on the anteroposterior image of the first bone, and acquiring the coordinate values of the plurality of pixel points in the lateral fracture boundary region of the first bone based on the lateral image of the first bone comprise:
- acquiring the anteroposterior fracture boundary region of the first bone based on the anteroposterior image of the first bone, and acquiring the lateral fracture boundary region of the first bone based on the lateral image of the first bone; and
- acquiring the coordinate values of the plurality of pixel points in the anteroposterior fracture boundary region of the first bone, and acquiring the coordinate values of the plurality of pixel points in the lateral fracture boundary region of the first bone; and acquiring the coordinate values of the plurality of pixel points in the anteroposterior fracture boundary region of the second bone based on the anteroposterior image of the second bone, and acquiring the coordinate values of the plurality of pixel points in the lateral fracture boundary region of the second bone based on the lateral image of the second bone comprise:
- acquiring the anteroposterior fracture boundary region of the second bone based on the anteroposterior image of the second bone, and acquiring the lateral fracture boundary region of the second bone based on the lateral image of the second bone; and
- acquiring the coordinate values of the plurality of pixel points in the anteroposterior fracture boundary region of the second bone, and acquiring the coordinate values of the plurality of pixel points in the lateral fracture boundary region of the second bone.

16. The device according to claim 15, wherein
acquiring the anteroposterior fracture boundary region of the first bone based on the anteroposterior image of the first bone, and acquiring the lateral fracture boundary region of the first bone based on the lateral image of the first bone comprise:
- acquiring an anteroposterior boundary region of the first bone based on the anteroposterior image of the first bone, and acquiring a lateral boundary region of the first bone based on the lateral image of the first bone; and
- selecting the anteroposterior fracture boundary region of the first bone from the anteroposterior boundary region of the first bone, and selecting the lateral fracture boundary region of the first bone from the lateral boundary region of the first bone; and acquiring the anteroposterior fracture boundary region of the second bone based on the anteroposterior image of the second bone, and acquiring the lateral fracture boundary region of the second bone based on the lateral image of the second bone comprise:
- acquiring an anteroposterior boundary region of the second bone based on the anteroposterior image of the second bone, and acquiring a lateral boundary region of the second bone based on the lateral image of the second bone; and
- selecting the anteroposterior fracture boundary region of the second bone from the anteroposterior boundary region of the second bone, and selecting the lateral fracture boundary region of the second bone from the lateral boundary region of the second bone.

17. A non-transitory storage medium storing at least one program code therein, wherein the program code, when loaded and executed by a processor, causes the processor to perform the computer-aided method for fracture reduction as defined in claim 1.

* * * * *